United States Patent [19]

Colson et al.

[11] 4,268,457

[45] May 19, 1981

[54] PROCESS FOR THE PREPARATION OF PARAPHENOXYBENZOYLCHLORIDE

[75] Inventors: James G. Colson, Williamsville; Victor F. G. Cooke, Youngstown; F. Howard Day; Michael J. Fifolt, both of Grand Island, all of N.Y.

[73] Assignee: Hooker Chemicals & Plastics Corp., Niagara Falls, N.Y.

[21] Appl. No.: 52,712

[22] Filed: Jun. 28, 1979

[51] Int. Cl.³ .................. C07C 51/093; C07C 41/22; C07C 43/275
[52] U.S. Cl. .................. 260/544 P; 568/639; 204/163 R
[58] Field of Search .................. 568/639; 260/544 P; 204/163 R

[56] References Cited

U.S. PATENT DOCUMENTS

| | | | |
|---|---|---|---|
| 2,214,768 | 9/1940 | Lincoln | 568/639 X |
| 2,464,877 | 3/1949 | Markarian et al. | 568/639 |
| 3,376,350 | 4/1968 | Wen | 568/639 |
| 4,108,904 | 8/1978 | Brown et al. | 568/639 X |

*Primary Examiner*—Bernard Helfin
*Attorney, Agent, or Firm*—Peter F. Casella; William J. Crossetta, Jr.; Arthur S. Cookfair

[57] ABSTRACT

The compound p-phenoxybenzotrichloride, useful as an intermediate in the preparation of various pesticides and monomers for the production of polyketone polymers, is prepared by the light-catalyzed reaction of p-phenoxytoluene with chlorine.

17 Claims, No Drawings

PROCESS FOR THE PREPARATION OF PARAPHENOXYBENZOYLCHLORIDE

BACKGROUND OF THE INVENTION

This invention relates to p-phenoxybenzotrichloride and to the preparation thereof. The compound p-phenoxybenzotrichloride is useful as a chemical intermediate in the preparation of various pesticides and polymers.

Aromatic polyketone polymers having excellent melt processability are described in U.S. Pat. No. 4,024,314. The preferred monomer for the preparation of such polyketone polymers is p-phenoxybenzoyl fluoride. This monomer is prepared by fluorination of p-phenoxybenzoyl chloride. Various methods for the preparation of p-phenoxybenzoyl chloride are known in the literature. In general the known method prior processes which may be employed in the preparation of p-phenoxybenzoyl chloride are multi-stepped processes which are costly and frequently complicated by the presence of undesirable impurities stemming from undesired side reactions or from the presence of reactants and/or catalysts employed.

It has now been found that p-phenoxybenzoyl chloride may be prepared in excellent yield and high purity by a novel process involving the use of a heretofore unknown compound, p-phenoxybenzotrichloride.

SUMMARY OF THE INVENTION

It has now been found that the novel compound p-phenoxybenzotrichloride may be prepared by a process which comprises the photo-chlorination reaction of p-phenoxytoluene with chlorine in the presence of a suitable non-reactive solvent. The compound p-phenoxybenzotrichloride, prepared in this manner, may be partially hydrolyzed by reaction with a suitable acid or by reaction with water, to produce p-phenoxybenzoylchloride. Thus in one aspect the present invention is directed to a novel compound, p-phenoxybenzotrichloride, and in a second aspect to a process for the preparation thereof. In still another aspect the present invention is directed to the preparation of p-phenoxybenzotrichloride as a step in the production of p-phenoxybenzoylchloride.

The preparation of p-phenoxybenzotrichloride is generally accomplished by irradiating mixtures of the reactants at the desired reaction temperatures until the desired degree of chlorination has been achieved. Reaction temperatures are generally in the range of from about 0° Celsius to about 180° Celsius and preferably in the range of from about 20° Celsius up to about the boiling point of the reaction mixture.

The reaction of chlorine with p-phenoxytoluene may be carried out neat or, preferably, in the presence of a non-reactive solvent. Suitable solvents include benzoic acid or a halogenated hydrocarbon solvent such as methylene chloride, chlorobenzene, polychlorinated benzenes and 1,1,2-trichloro-1,2,2-trifluoroethane, which tend to moderate or facilitate the reaction. A preferred solvent for this purpose is carbon tetrachloride. It has been found that when carbon tetrachloride is employed as a solvent in the present reaction the tendency toward undesired ring chlorination is lessened.

Typically the reaction is carried out by the addition of chlorine gas or sulfuryl chloride, with or without suitable catalyst to a suitably heated liquid reaction medium comprising p-phenoxytoluene in carbon tetrachloride solvent. It has been found that undesired ring chlorination may occur as full conversion of the p-phenoxybenzotrichloride intermediate is approached. Accordingly, maximum yields and product purity are achieved by carefully following the progress of the reaction and stopping the addition of chlorine before extensive ring chlorination occurs.

Actinic light is employed for promoting the chlorination reaction. Any of the well known light sources which will accelerate the chlorination of p-phenoxytoluene may be used, such as tungsten filament lamps, ultraviolet lamps, mercury vapor arc lamps, fluorescent lamps, ordinary light bulbs, and the like. The preferred irradiation is an ultraviolet light source.

The compound p-phenoxybenzotrichloride is a white crystalline solid at ordinary temperatures, having a melting point of about 48°–49.50° Celsius, and thus is readily purified by fractional crystallization and distillation.

The crystallization can be achieved by partial crystallization of the neat material or by crystallization from a suitable solvent. Distillation is preferably run under reduced pressure.

The p-phenoxybenzotrichloride may be partially hydrolyzed to form p-phenoxybenzoylchloride in high yields. The hydrolyzation can be affected by a hydroxy donating system, catalyzed or non-catalyzed, which donates an oxygen by replacement of two of the chlorines from the trichloromethyl group without forming an adduct with the desired acid chlorine product. The following compounds have been found effective in hydrolyzing p-phenoxybenzotrichloride to p-phenoxybenzoylchloride: organic acids, including substituted and unsubstituted aliphatic mono- and di-carboxylic acids, such as acetic, propionic, butyric, maleic, adipic, gluteric and malonic acids as well as substituted and unsubstituted aromatic mono- and di-carboxylic acids such as benzoic, p-phenoxybenzoic, terephthalic, isophthalic and phthalic acids; aqueous mineral acids, such as hydrochloric, hydrobromic, hydroiodic and hydrofluoric acids as well as dilute sulfuric and phosphoric acids; water; sulfuric acids such as methane sulfonic acid, benzene sulfonic acid, toluene sulfonic acid and the like; mixtures of Lewis acids, e.g. ferric chloride, aluminum chloride and zinc chloride, with water and/or the afore identified organic acids; and, mixtures thereof. Thus, in one embodiment, p-phenoxybenzotrichloride is contacted with an approximately equimolar amount of water. The amount of water may vary somewhat but is preferably within about 10% of the equimolar amount. Lesser amounts will result in lower yields of the p-phenoxybenzoylchloride and greater amounts will result in a degree of hydrolysis to p-phenoxybenzoic acid. The reaction may be carried out at temperatures of about room temperature (about 20° Celsius) and higher and will proceed most readily with external heat at a temperature in excess of about 100° Celsius and preferably at a temperature in the range of about 130° to about 150° Celsius. Under autogenous pressure higher temperature may be employed, however, temperatures in excess of about 180° Celsius provide little advantage and are not preferred. In a preferred mode it has been found that the incorporation of hydrochloric acid in the starting reaction medium, facilitates partial hydrolysis reaction with the unexpected advantage of less stringent temperature requirements. The amount of hydrochloric acid employed, based on hydrogen chloride content, may vary considerably. Conveniently, concentrated hydrochloric acid is employed in an amount sufficient to provide the desired molar amounts of water. Lesser strengths of hydrochloric acid may be employed if desired. Preferred temperature in this mode is in the range of about 70° to about 110° Celsius.

Alternatively the partial hydrolysis of p-phenoxybenzotrichloride may be effected by reaction with a mono- or di-carboxylic acid to produce a mixture of p-phenoxybenzoylchloride and an acid chloride derived from the carboxylic acid employed. A wide variety of carboxylic acids may be employed including both aliphatic and aromatic carboxylic acids. The reaction proceeds to high yields in an unexpectedly facile manner at ambient temperature and without the need for a catalyst. Higher temperatures may be employed but are not required. In a particularly advantageous mode, p-phenoxybenzoic acid is employed as the carboxylic acid with the result that no co-product is formed since both reactants are converted in the reaction to the desired product p-phenoxybenzoylchloride.

The proportions of carboxylic acid employed may vary, but are preferably within about 10% of the equimolar amount based on the p-phenoxybenzotrichloride reactant.

In one mode of the invention the p-phenoxybenzotrichloride was completely hydrolyzed with water alone, or an aqueous base such as KOH, and a suitable co-solvent such as acetone or isopropyl alcohol to form the p-phenoxybenzoic acid, or salt thereof (which may then be neutralized to the acid), and then chlorinated, for example with thionyl chloride, to form the desired p-phenoxybenzoyl chloride.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLE 1—Preparation of P-Phenoxybenzotrichloride

Ten parts of p-phenoxytoluene containing about 0.2% of N,N-dimethyl caproamide (a sequestering agent to remove any traces of iron) was charged to a reaction vessel and heated to about 120° C. The temperature was maintained at about 120° C. while the reaction mixture was irradiated with a mercury arc lamp and approximately 12 parts of chlorine were sparged into the mixture over a period of 4 hours. The progress of the reaction was monitored with periodic sampling and analysis and the chlorine flow was stopped when over-chlorination (i.e., ring chlorination) was observed. Product samples were treated with $CaO/Na_2S_2O_2$, filtered, and analyzed by gas chromatographic techniques. The yield of p-phenoxybenzotrichloride was 20% based on p-phenoxytoluene starting material.

EXAMPLE 2—Preparation of P-Phenoxybenzotrichloride

A mixture of 5.0 parts of p-phenoxytoluene and 0.02 parts of N,N-dimethyl caproamide in 21.53 parts of carbon tetrachloride was charged to a reaction vessel and heated to about 95° C. The reaction mixture was irradiated with a mercury arc lamp and the temperature maintained at about 95° C. while about 54 parts of chlorine were sparged into the mixture over a period of about 3.5 hours. The progress of the reaction was monitored by periodic sampling and analysis and the chlorine flow was stopped when over-chlorination was observed. Product samples were treated with $CaO/Na_2S_2O_2$, filtered and analyzed by gas chromatographic techniques. The yield of p-phenoxybenzotrichloride, was greater than 70%, based on p-phenoxytoluene starting material.

Samples of the p-phenoxybenzotrichloride prepared by the methods of Examples 1 and 2 were purified by fractional crystallization from heptane and acetonitrile. The purified samples were characterized by a melting point of about 48°–49.50° C. and mass spectural data confirmed a molecular structure of $C_{13}H_9Cl_3O$.

EXAMPLE 3—Preparation of P-Phenoxybenzoylchloride

A mixture of 5.75 parts of p-phenoxybenzotrichloride and 0.36 parts of water was charged to a reaction vessel and gradually heated. Reaction was observed to occur as the temperature of the mixture approached 120° C. with a rapid increase as the temperature approached 140° C. The reaction mixture was maintained at about 140° C. for about one hour, then vacuum stripped and the product analyzed by gas chromatographic techniques. Analysis (in area percent) indicated 83% p-phenoxybenzoylchloride and 9% of the p-phenoxybenzotrichloride starting material.

EXAMPLE 4—Preparation of P-Phenoxybenzoylchloride

A mixture of 5.75 parts of p-phenoxybenzotrichloride and 0.58 parts of concentrated (37%) hydrochloric acid (containing 0.36 parts of water) was charged to a reaction vessel and heated slowly. As the temperature approached 78° C., reaction was observed with evolution of HCl. Continued heating at temperatures of about 80°–85° C., was maintained for about two hours. Analysis of the product by gas chromatographic techniques indicated 36.0% of p-phenoxybenzoylchloride and 24.5% of p-phenoxybenzotrichloride starting material.

EXAMPLE 5—Preparation of P-Phenoxybenzoylchloride

P-phenoxybenzotrichloride (288 parts) was added to 182 parts of p-phenoxybenzoic acid, with mixing. The mixture was allowed to stand at ambient temperature for about 16 hours, then heated, over a period of about 4 hours, to a temperature of about 140° C., at which point HCl evolution was detected. The mixture was maintained at a temperature of between about 112° and 140° C. for an additional 21 hours, then cooled and analyzed by gas chromatographic techniques. Analysis indicated a 73% yield of p-phenoxybenzoylchloride based on the starting materials.

EXAMPLE 6—Preparation of P-Phenoxybenzoylchloride

A mixture of 5.75 parts of p-phenoxybenzotrichloride and 2.44 parts of benzoic acid was charged to a reaction vessel and heated to about 140° C. over a period of about one hour, at which point the evolution of HCl from the reaction mixture was observed. The mixture was maintained at about 120° to about 140° C. for an additional hours, then cooled and analyzed by gas chromatographic techniques. Analysis indicated 19.9% p-phenoxybenzoylchloride, and 8.3% benzoylchloride.

EXAMPLE 7—Preparation of P-Phenoxybenzoylchloride

Acetic acid (2.1 parts) was mixed with p-phenoxybenzotrichloride (10 parts) and the mixture was allowed to stand at ambient conditions for about 64 hours. Analysis of the mixture by $C^{13}$ NMR analysis, in relative mole %, indicated 68% p-phenoxybenzoylchloride and 19% p-phenoxybenzotrichloride.

What is claimed is:

1. p-phenoxybenzotrichloride.
2. A process for the preparation of p-phenoxybenzoylchloride which comprises reacting p-phenoxybenzotrichloride with a hydrolyzing reactant selected from water, aqueous mineral acids, carboxylic acids, sulfonic acids, mixtures of lewis acids with water or carboxylic acids and mixtures thereof.
3. A process according to claim 2 wherein said hydrolyzing reactant is water.
4. A process according to claim 3 wherein the molar ratio of water:p-phenoxybenzotrichloride is about 0.9:1 to about 1.1:1.
5. The process according to claim 2 wherein said hydrolyzing reactant is an aqueous mineral acid selected from hydrochloric hydrobromine, hydroiodic, hydrofluoric and dilute sulfuric and phosphoric acids.
6. A process according to claim 2 wherein said hydrolyzing reactant is aqueous hydrochloric acid.
7. A process according to claim 6 wherein the water present in the hydrochloric acid is sufficient to provide a molar ratio of water:p-phenoxybenzotrichloride of about 0.9:1 to about 1.1:1.
8. A process according to claim 7 wherein the hydrochloric acid is concentrated hydrochloric acid.
9. A process according to claim 2 wherein said hydrolyzing reactant is a carboxylic acid.
10. A process according to claim 9 wherein the carboxylic acid is present in a molar ratio of carboxylic acid:p-phenoxybenzotrichloride of about 0.9:1 to about 1.1:1.
11. A process according to claim 9 wherein said carboxylic acid is selected from the group consisting of substituted and unsubstituted acetic, propionic, butyric, maleic, adipic, gluteric, malonic, benzoic, p-phenoxybenzoic, terephthalic, isophthalic and phthalic acids.
12. A process according to claim 10 wherein the carboxylic acid is acetic acid.
13. A process according to claim 10 wherein the carboxylic acid is benzoic acid.
14. A process according to claim 10 wherein the carboxylic acid is p-phenoxybenzoic acid.
15. A process for the preparation of p-phenoxybenzoylchloride which comprises reacting p-phenoxytoluene with chlorine in the presence of actinic light to produce a product containing p-phenoxybenzotrichloride and thereover hydrolyzing said p-phenoxybenzotrichloride with a hydrolysis reactant selected from water, aqueous mineral acid, carboxylic acid, mixtures of lewis acids with water or carboxylic acids and mixtures thereof to produce a p-phenoxybenzoyl chloride product.
16. The process of claim 15 wherein said product containing p-phenoxybenzotrichloride is separated from the reaction solution prior to hydrolysis.
17. The process of claim 16 wherein said separation is by crystallization or distillation.

* * * * *